United States Patent [19]

Scharf et al.

[11] 4,292,246

[45] Sep. 29, 1981

[54] PREPARATION OF TETRAHYDROFURAN-3-ALDEHYDES

[75] Inventors: Hans-Dieter Scharf, Roetgen; Herbert Fraüenrath, Aachen, both of Fed. Rep. of Germany

[73] Assignee: Bayer Aktiengesellschaft, Leverkusen, Fed. Rep. of Germany

[21] Appl. No.: 108,308

[22] Filed: Dec. 31, 1979

[30] Foreign Application Priority Data

Jan. 17, 1979 [DE] Fed. Rep. of Germany ....... 2901644

[51] Int. Cl.$^3$ ................. C07D 307/12; C07D 307/24; C07D 307/94
[52] U.S. Cl. ............................. 260/347.4; 260/347.5; 260/347.8; 260/347.9
[58] Field of Search ............... 260/347.4, 347.5, 347.8, 260/347.9

[56] References Cited

PUBLICATIONS

Thuy, C. R., Acad. Sc., Paris, Ser. C, vol. 273, (1971), pp. 1655–1657.

*Primary Examiner*—Richard Raymond
*Attorney, Agent, or Firm*—Sprung, Felfe, Horn, Lynch & Kramer

[57] ABSTRACT

A process for the preparation of a tetrahydrofuran-3-aldehyde of the formula

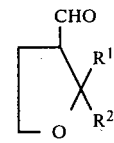

in which
$R^1$ is hydrogen, or an alkyl or phenyl radical, and
$R^2$ is an alkyl, ($C_1$–$C_4$-alkoxy)-carbonyl, ($C_1$–$C_4$-alkoxy) carbonylmethylene or phenyl radical, or
$R^1$ and $R^2$ together are an alkanediyl radical, comprising heating a 4,5-dihydro-1,3-dioxepine of the formula

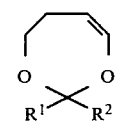

at about 100° to 250° C. in the presence of a catalytic amount of o-toluic acid. Advantageously about 0.05 to 0.15 mole of o-toluic acid is used per mole of the dioxepine, and heating is effected between about 120° and 200° C. at a pressure up to about 10 bars. The compounds, some of which are new, are insecticidally and acaricidally active.

7 Claims, No Drawings

PREPARATION OF TETRAHYDROFURAN-3-ALDEHYDES

The invention relates to an unobvious process for the preparation of certain tetrahydrofuran-3-aldehydes.

It is known that under base catalysis 4,7-dihydro-1,3-dioxepines isomerize to 4,5-dihydro-1,3-dioxepines. However, under the customary reaction conditions—heating with potassium tert.-butylate in tert.-butanol—it is not 2-(4-methoxy-phenyl)-4,5-dihydro-1,3-dioxepine which forms from 2-(4-methoxy-phenyl)-4,7-dihydro-1,3-dioxepine, but 2-(4-methoxy-phenyl)-tetrahydrofuran-3-aldehyde. Experimental details and product characteristics for this reaction are not known (see C.R. Acad. Sci. Ser. C 273 (1971), 1655–1657).

The present invention now provides a process for the preparation of a tetrahydrofuran-3-aldehyde of the general formula

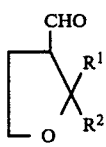

(I), in which
R$^1$ represents hydrogen, alkyl or optionally substisubstituted phenyl and
R$^2$ represents optionally substituted alkyl, (C$_{1-4}$-alkoxy)-carbonyl, (C$_{1-4}$-alkoxy)-carbonylmethylene or optionally substituted phenyl or
R$^1$ and R$^2$ together represent alkanediyl,
in which a 4,5-dihydro-1,3-dioxepine of the general formula

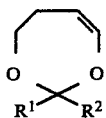

(II), in which
R$^1$ and R$^2$ have the meanings indicated above, is heated with a catalytic amount of o-toluic acid to a temperature of between 100° and 250° C.

Surprisingly, tetrahydrofuran-3-aldehydes can be prepared in very good yields by the process according to the invention by acid-catalyzed isomerization of 4,5-dihydro-1,3-dioxepines. This was not to be expected according to the prior art.

Some of the tetrahydrofuran-3-aldehydes obtainable by the process according to the invention are new. They all have powerful insecticidal and acaricidal properties.

The invention is preferably applied to the preparation of compounds of the formula (I) in which
R$^1$ represents hydrogen, straight-chain or branched alkyl with 1 to 4 carbon atoms or phenyl and
R$^2$ represents straight-chain or branched alkyl with 1 to 4 carbon atoms, methoxycarbonyl, ethoxycarbonyl, methoxycarbonylmethylene or ethoxycarbonylmethylene or represents phenyl which is optionally substituted by C$_{1-4}$-alkoxy, or
R$^1$ and R$^2$ together represent straight-chain or branched α,ω-alkanediyl with 3 to 9 carbon atoms.

If the starting compound used is, for example, 2-ethyl-2-phenyl-4,5-dihydro-1,3-dioxepine, the reaction according to the invention can be represented by the following equation:

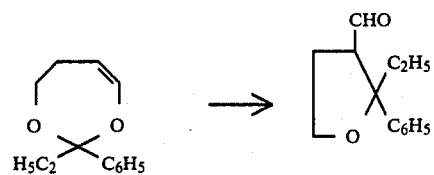

The 4,5-dihydro-1,3-dioxepines to be used as starting materials are defined by formula (II).

In this formula, R$^1$ and R$^2$ preferably have those meanings which have been mentioned as preferred in connection with the definition of R$^1$ and R$^2$ in formula (I).

Examples which may be mentioned of the starting compounds of the formula (II) are: 2-methyl-, 2-ethyl-, 2-phenyl-, 2,2-diphenyl-, 2-(4-methoxyphenyl)-, 2-methyl-2-carbethoxy-, 2-methyl-2-carbethoxy-methylene-, 2,2-dimethyl-, 2,2-diethyl-, 2-methyl-2-ethyl-, 2-methyl-2-phenyl- and 2-ethyl-2-phenyl-4,5-dihydro-1,3-dioxepine and also 7,12-dioxaspiro[5.6]dodec-8-ene.

Some of the 4,5-dihydro-1,3-dioxepines of the formula (II) are known (see C. R. Acad. Sci. Ser. C 273 (1971), 1655–1657). They can all be obtained by base-catalyzed isomerization of 4,7-dihydro-1,3-dioxepines of the general formula

(III), in which R$^1$ and R$^2$ have the meanings indicated above, in general by heating in the presence of 0.1 to 2, preferably 0.1 to 1.5 mol equivalents of a base, for example potassium tert.-butylate, and optionally with the use of a solvent or diluent, for example tert.-butanol or dimethylsulphoxide, to temperatures of between 20° and 200° C. and preferably between 50° and 150° C. Working up can be effected in a conventional manner, for example by pouring the reaction mixture, after cooling, into ice-water, extracting the resulting mixture with a water-immiscible solvent, for example diethyl ether, washing and drying the organic phase and, after filtering, distilling off the solvent and purifying the residual product by distillation.

4,7-Dihydro-1,3-dioxepines of the formula (III) are known (see Bull. Soc. Chim. France 1975, 1763–1766 and 2558–2560 and U.S. Pat. No. 3,116,298) and can be prepared analogously to known processes.

Preferred starting compounds are compounds of the formula (III) in which R$^1$ and R$^2$ have the meanings indicated as being preferred in the definition of R$^1$ and R$^2$ in formula (I).

Examples which may be mentioned are: 2-methyl-, 2-ethyl-, 2-phenyl-, 2,2,-diphenyl-, 2-methyl-2-carbethoxy-, 2-methyl-2-carbethoxymethylene-, 2-(4-methoxy-phenyl)-2,2-dimethyl-, 2,2-diethyl-, 2-methyl-2-ethyl-, 2-methyl-2-phenyl- and 2-ethyl-2-phenyl-4,7-dihydro-1,3-dioxepine and also 7,12-dioxaspiro[5.6]dodec-9-ene.

When carrying out the process according to the invention, about 0.01 to 0.2 mol and preferably about 0.05 to 0.15 mol of o-toluic acid are employed as the catalyst, per mol of 4,5-dihydro-1,3-dioxepine. In general, the reactants are added together at room temperature and heated for several hours at a temperature of between 100° and 250° C. and preferably of between 120° and 200° C. The reaction is carried out under normal pressure or slightly elevated pressure, in general under 1 to 10 bars. After the end of the reaction, the tetrahydrofuran-3-aldehydes are distilled off from the reaction mixture and optionally purified by a further fractional distillation. The refractive index is used to characterize the products.

The invention also provides certain new tetrahydrofuran-3-aldehydes falling under the formula (I).

As already mentioned, the compounds according to the present invention are distinguished by an excellent insecticidal and acaricidal activity. They are therefore active against plant pests, pests harmful to health and pests of stored products. The above-mentioned pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Recticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the order of the Acarina, for example *Acarus siro,* Argas spp., Ornithodoros spp., *Dermanyssus gallinae, Eriophytes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as good stability to alkali on limed substrates.

The present invention also provides an insecticidal or acaricidal composition containing as active ingredient a compound of the present invention in admixture with a solid or liquefied gaseous diluent or carrier or in admixture with a liquid diluent or carrier containing a surface-active agent.

The present invention also provides a method of combating insects or acarids which comprises applying to the insects or acarids, or to a habitat thereof, a compound of the present invention alone or in the form of a composition containing as active ingredient a compound of the present invention in admixture with a diluent or carrier.

The present invention further provides crops protected from damage by insects or acarids by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLE

EXAMPLE 1

(A) The 4,5-dihydro-1,3-dioxepines which are to be used as starting compounds could be prepared as follows:

(a)

In a 1 liter three-necked flask fitted with a stirrer and a reflux condenser with a drying tube, 88.1 g (0.5 mol) of 2-phenyl-4,7-dihydro-1,3-dioxepine were allowed to run dropwise in the course of one hour into a suspension of 67.3 g (0.6 mol) of potassium tert.-butylate in 300 ml of absolute dimethylsulphoxide. After the exothermic reaction had subsided, the mixture was heated at 80° C. for 48 hours, while stirring.

The mixture was then allowed to cool to room temperature and the dark brown reaction mixture was poured into 500 ml of ice-water, while stirring. In order to extract the organic phase the aqueous phase was shaken first with 500 ml of diethyl ether and then several times with, in each case, 100 ml of diethyl ether. The combined ether phases were washed three times with 200 ml of saturated sodium chloride solution and dried over anhydrous potassium carbonate. After filtering off the desiccant, the solvent was distilled off and the crude product was purified by distillation. 51.1 g (58% of theory) of 2-phenyl-4,5-dihydro-1,3-dioxepine with a boiling point of 63°–64.5° C./0.001 mm Hg and a refractive index $n_D^{20}$ of 1.5470 were obtained in the form of a colorless liquid.

The following compounds of the formula (II)

(II)

could be prepared analogously:

TABLE A

| Intermediate | $R^1$ | $R^2$ | Yield (% of theory) | Refractive index ($n_D^{20}$) | Boiling point (°C./mm Hg) |
|---|---|---|---|---|---|
| b | H | p-$C_6H_4$—$OCH_3$ | 67 | 1.5600 | 86–87/0.01 |

TABLE A-continued

| Inter-mediate | R¹ | R² | Yield (% of theory) | Refractive index ($n_D^{20}$) | Boiling point (°C./mm Hg) |
|---|---|---|---|---|---|
| c | CH₃ | CH₃ | 60 | 1.4440 | 33/34/12 |
| d | CH₃ | C₂H₅ | 66 | 1.4475 | 53.5-55/15 |
| e | CH₃ | C₆H₅ | 72 | 1.5295 | 57.5-68.5/0.001 |
| f | —CH₂CH₂CH₂CH₂CH₂— | | 72 | 1.4843 | 95.5-96/15 |

(B)

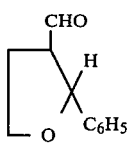

(1)

3 g of o-toluic acid were added to 44 g (0.25 mol) of 2-phenyl-4,5-dihydro-1,3-dioxepine and the mixture was heated at 150° C. for 3 hours, while stirring. The 2-phenyltetrahydrofuran-3-aldehyde which had formed (a mixture of the cis and trans isomers) was then distilled under reduced pressure.

Yield: 33.9 g (77% of theory); colorless liquid; boiling point 81° C./0.001 mm Hg; refractive index $n_D^{20}$ 1.5395.

The following compounds of the formula

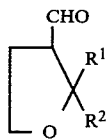

(I)

could be prepared analogously:

TABLE B

| Compound No. | R¹ | R² | Yield (% of theory) | Refractive index ($n_D^{20}$) | Boiling Point (°C./mm Hg) |
|---|---|---|---|---|---|
| 2 | H | p-C₆H₄—OCH₃ | 70 | 1.5498 | 114-116/0.001 |
| 3 | CH₃ | CH₃ | 95 | 1.4418 | 58.5-60/12 |
| 4 | CH₃ | C₂H₅ | 90 | 1.4490 | 75-76.5/12 |
| 5 | CH₃ | C₆H₅ | 92 | 1.5410 | 88-90/0.5 |
| 6 | —CH₂CH₂CH₂CH₂CH₂— | | 95 | 1.4840 | 122.5-123.5/15 |
| 7 | H | CH₃ | 15 | cis: 1.4425 trans: 1.4450 | cis: 82-83/100 trans: 75-80/100 |
| 8 | C₆H₅ | C₆H₅ | | | |
| 9 | CH₃ | —CO₂C₂H₅ | | | |
| 10 | CH₃ | —CH₂—COOC₂H₅ | | | |

It will be appreciated that the instant specification and examples are set forth by way of illustration and not limitation, and that various modifications and changes may be made without departing from the spirit and scope of the present invention.

What is claimed is:

1. A process for the preparation of a tetrahydrofuran-3-aldehyde of the formula

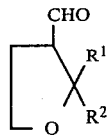

in which

R¹ is hydrogen, or an alkyl or phenyl radical, and

R² is an alkyl, (C₁–C₄-alkoxy)-carbonyl, (C₁₋₄-alkoxy)-carbonylmethylene or phenyl radical, or R¹ and R² together are an alkanediyl radical, comprising heating a 4,5-dihydro-1,3-dioxepine of the formula

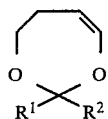

at about 100° to 250° C. in the presence of a catalytic amount of o-toluic acid.

2. A process according to claim 1, in which

R¹ is hydrogen, alkyl with 1 to 4 carbon atoms, or phenyl, and

R² is alkyl with 1 to 4 carbon atoms, methoxy-carbonyl, ethoxy-carbonyl, methoxycarbonylmethylene or ethoxycarbonylmethylene, phenyl, or C₁₋₄-alkoxyphenyl, or R¹ and R² together are α,ω-alkanediyl with 3 to 9 carbon atoms.

3. A process according to claim 1 in which about 0.01 to 0.2 mole of o-toluic acid is used per mole of the dioxepine.

4. A process according to claim 3, in which about 0.05 to 0.15 mole of o-toluic acid is used per mole of the dioxepine.

5. A process according to claim 1, in which the heating is effected between about 120° and 200° C.

6. A process according to claim 1, in which the heating is effected at a pressure from normal pressure up to about 10 bars.

7. A process according to claim 2, in which about 0.05 to 0.15 mole of o-toluic acid is used per mole of the dioxepine, and heating is effected between about 120° and 200° C. at a pressure up to about 10 bars.

* * * * *